US005545615A

United States Patent [19]

Maraganore

[11] Patent Number: 5,545,615
[45] Date of Patent: Aug. 13, 1996

[54] A METHOD OF INHIBITING FERTILIZATION BY ALPHA-1-ANTITRYPSIN OR ANTITHROMBIN III

[75] Inventor: John M. Maraganore, Waltham, Mass.

[73] Assignee: ZymoGenetics, Inc., Seattle, Wash.

[21] Appl. No.: 312,010

[22] Filed: Sep. 22, 1994

Related U.S. Application Data

[63] Continuation of Ser. No. 73,975, Jun. 8, 1993, abandoned, which is a continuation of Ser. No. 944,818, Sep. 14, 1992, abandoned, which is a continuation of Ser. No. 821,273, Jan. 10, 1992, abandoned, which is a continuation of Ser. No. 610,459, Nov. 8, 1990, abandoned, which is a continuation of Ser. No. 98,264, Sep. 18, 1987, abandoned.

[51] Int. Cl.$^6$ .................................................. A61K 37/02
[52] U.S. Cl. ............................. 514/2; 514/21; 514/843; 424/DIG. 14
[58] Field of Search ................................. 424/520, 529, 424/530, 430, DIG. 14; 514/2, 21

[56] References Cited

U.S. PATENT DOCUMENTS

| | | | |
|---|---|---|---|
| 3,875,300 | 4/1975 | Homm et al. | 424/433 |
| 4,368,186 | 1/1983 | Vickery et al. | 574/399 |
| 4,384,003 | 5/1983 | Kazmiroski et al. | 514/718 |
| 4,469,671 | 9/1984 | Zimmerman et al. | 424/432 |
| 4,589,880 | 5/1986 | Dunn et al. | 128/832 |

OTHER PUBLICATIONS

Allen et al., *AJCP* 62: 732–739, 1974.
Fagerhol and Laurell, *Prog. Med. Genet.* 7:96–111, 1970.
Yang et al., *Fertility and Sterility* 27: 577–581, 1976.
Bhattacharyya et al., *J. Reprod. Fert.* 47:97–100, 1976.
Fritz et al., *Hoppe–Seyler's Z. Physiol. Chem.* Bd. 353:1950–1952, 1972.
Fritz et al., *Hoppe–Seyler's Z. Physiol. Chem.* Bd. 353:1953–1956, 1972.

*Primary Examiner*—Marian C. Knode
*Assistant Examiner*—Jean C. Witz
*Attorney, Agent, or Firm*—Debra K. Leith; Gary E. Parker; Deborah A. Sawislak

[57] ABSTRACT

Methods for inhibiting fertilization in warm-blooded animals are disclosed. The methods generally comprise administering to the animal an effective amount of a composition comprising a protein that forms a covalent complex with acrosin, and a physiologically acceptable carrier or diluent. Suitable proteins for use in the methods include members of the serpin family of proteins, such as alpha-1-antitrypsin.

6 Claims, 2 Drawing Sheets

A METHOD OF INHIBITING FERTILIZATION BY ALPHA-1-ANTITRYPSIN OR ANTITHROMBIN III

CROSS-REFERENCE TO RELATED APPLICATION

This application is a continuation of U.S. patent application Ser. No. 08/073,975, filed Jun. 8, 1993, now abandoned, which is a continuation of Ser. No. 07/944,818, filed Sep. 14, 1992, now abandoned, which is a continuation of Ser. No. 07/821,273, filed Jan. 10, 1992, now abandoned, which is a continuation of Ser. No. 07/610,459, filed Nov. 8, 1990, now abandoned, which is a continuation of Ser. No. 07/098,264, filed Sep. 18, 1987, now abandoned.

TECHNICAL FIELD

The present invention relates to methods for inhibiting fertilization of warm-blooded animals in general, and more specifically, to the use of topical contraceptive compositions for inhibiting fertilization.

BACKGROUND ART

A variety of compositions and devices have been used in an effort to inhibit fertilization. Among the contraceptives presently in use are spermicides or inhibitors of sperm function. Of these, the most commonly used are cytotoxic agents, such as nonoxynol-9, a nonionic surfactant. In addition, the use of agents which inhibit enzymes necessary for sperm function has also been addressed. One enzyme which has been targeted for contraceptive action is acrosin. Acrosin is a 38,000 Da plasmin- or trypsin-like proteinase found in the acrosomes of mammalian spermatozoa which degrades the zona pellucida of the ovum, a glyco-proteinaceous wall which must be broken for fertilization to occur. Acrosin activity is absent from newly ejaculated sperm but appears on the spermatozoa in the female reproductive tract after "capacitation," a process by which sperm achieve the ability to penetrate the ovum. The capacitation process involves activation of acrosin and other proteinases, apparently through the removal of enzyme inhibitors present in the Seminal plasma. Release of proteinase inhibitors from the cortical granules of the ovum following fertilization may act as a block to polyspermy (Conrad et al., *J. Reprod. Fert.* 27: 133–135, 1971). These processes are reviewed by McRorie et al. (*Ann. Rev. Biochem.* 43: 777, 1974); Hafez, ed. (*Human Semen and Fertility Regulation in Men*, C. V. Mosby Co., St. Louis, Mo., 1976, pp. 201–242 and 563–582); and Zaneveld et al. (*Proc. Soc. Exp. Biol. Med.* 133: 1172, 1970).

Certain inhibitors of acrosin have been shown to prevent fertilization in vitro, but only a limited number of these are useful as contraceptives. The use of non-protein proteinase inhibitors, including acrosin inhibitors, in intravaginal or intrauterine contraceptive devices is disclosed by Zimmerman et al. (U.S. Pat. Nos. 4,264,575; 4,264,576; 4,264,577; 4,493,699; and 4,469,671). The proteinase inhibitors disclosed are cationic surfactant salts, such as cationic salts of various carboxylic and sulfonic, sulfuric, or phosphoric acids of relatively high molecular weight hydrocarbon moieties. The nature of the interaction(s) between these compounds and the target enzymes is not disclosed. In vitro treatment of capacitated rabbit sperm with pancreatic trypsin inhibitor or partially purified seminal plasma inhibitor inhibited fertilization when the treated sperm were introduced into the oviducts of female rabbits via injection (Zaneveld et al., *J. Reprod. Fert.* 225: 387–392, 1971). Zaneveld et al. (*FEBS Lett.* 11: 345–347, 1970) demonstrated that soybean and lima bean trypsin inhibitors block acrosin activity and prevent fertilization in vitro. They also demonstrated the use of the non-protein acrosin inhibitor tosyl-L-lysine chloromethyl ketone (TLCK) as a vaginal contraceptive in rabbits.

In contrast to non-protein proteinase inhibitors, naturally-occurring protein proteinase inhibitors associate reversibly with their substrates (Tschesche, *Angew. Chem. Int. Ed. Eng.* 13: 10–28, 1974, and Zaneveld et al., 1970, ibid.) and would therefore not be expected to be effective as contraceptive agents given that the normal process of sperm capacitation in the female reproductive tract involves the removal of protein inhibitors of acrosin.

One such naturally-occurring protein is alpha-1-antitrypsin (also known as alpha-1-proteinase inhibitor), which has been shown to inhibit human and boar acrosin in vitro (Fritz et al., *Hoppe-Seyler's Z. Physiol Chem.* 343: 1950–1952 and 1953–1956, 1972). Since this inhibitor is generally believed to function through competitive (reversible) inhibition of the substrate (Carrell et al., *Nature* 298: 329–334, 1982), it would riot be expected to be suitable for contraceptive use. Furthermore, cervical secretions of human females have been shown to contain inhibitors of trypsin and chymotrypsin (Haendle et al., *Hoppe-Seyler's Z. Physiol. Chem.* 351: 545–546, 1970).

During the decade 1973–1982 (the most recent period for which extensive data are available), the use of oral contraceptives among women in the United States sharply declined (Bachtach, *Fam. Plann. Perspect.* 16: 253–259, 1984). This may be traced, at least in part, to complications associated with the use of oral contraceptives, including an increased risk of cancer, blood clots, and associated disorders. Use of "the pill" has therefore been supplanted by use of less effective barrier methods, such as condoms, diaphragms, and foams and by sterilization. Another alternative, the intrauterine device (IUD), has also been associated with health risks to the user. Many of these devices have been withdrawn from the marketplace. The traditional barrier methods often rely in part on spermicidal agents for their effectiveness. In general, only a limited number of sperm-inhibiting compounds have proven to be acceptable as contraceptive agents. The most widely used spermicidal agents are harsh, cytotoxic chemicals which may cause irritation or allergic reactions in users. Further, it has been suggested that the toxic effects of these agents on sperm may lead to birth defects when partially impaired sperm fertilize the ovum.

There is thus a need for impermanent, dependable methods of contraception which are not associated with the health risks to the user or her offspring described above. The present invention provides such a method while further providing other related advantages.

DISCLOSURE OF THE INVENTION

Briefly stated, the present invention discloses a method for inhibiting fertilization in warm-blooded animals. The method generally comprises administering to the animal an effective amount of a composition comprising a protein that forms a covalent complex with acrosin, and a physiologically acceptable carrier or diluent. It is preferable, in this regard, to utilize a member of the serpin family of proteins. In one particular preferred aspect of the present invention, the protein is alpha-1-antitrypsin.

Within a related aspect of the present invention, the protein is antithrombin III or tissue plasminogen activator inhibitor. Suitable carriers or diluents for use in combination with the proteins described above include polyethylene glycol and polyoxyethylene-polyoxypropylene block copolymers.

Other aspects of the present invention will become evident upon reference to the following detailed description and attached drawings.

BRIEF DESCRIPTION OF THE DRAWINGS

FIG. 2, sperm capacitation in control medium, fertilization in AAT-containing medium; fertilization in control medium; FIG. 4, capacitation and fertilization in AAT-containing medium.

BEST MODE FOR CARRYING OUT THE INVENTION

Figure 1:
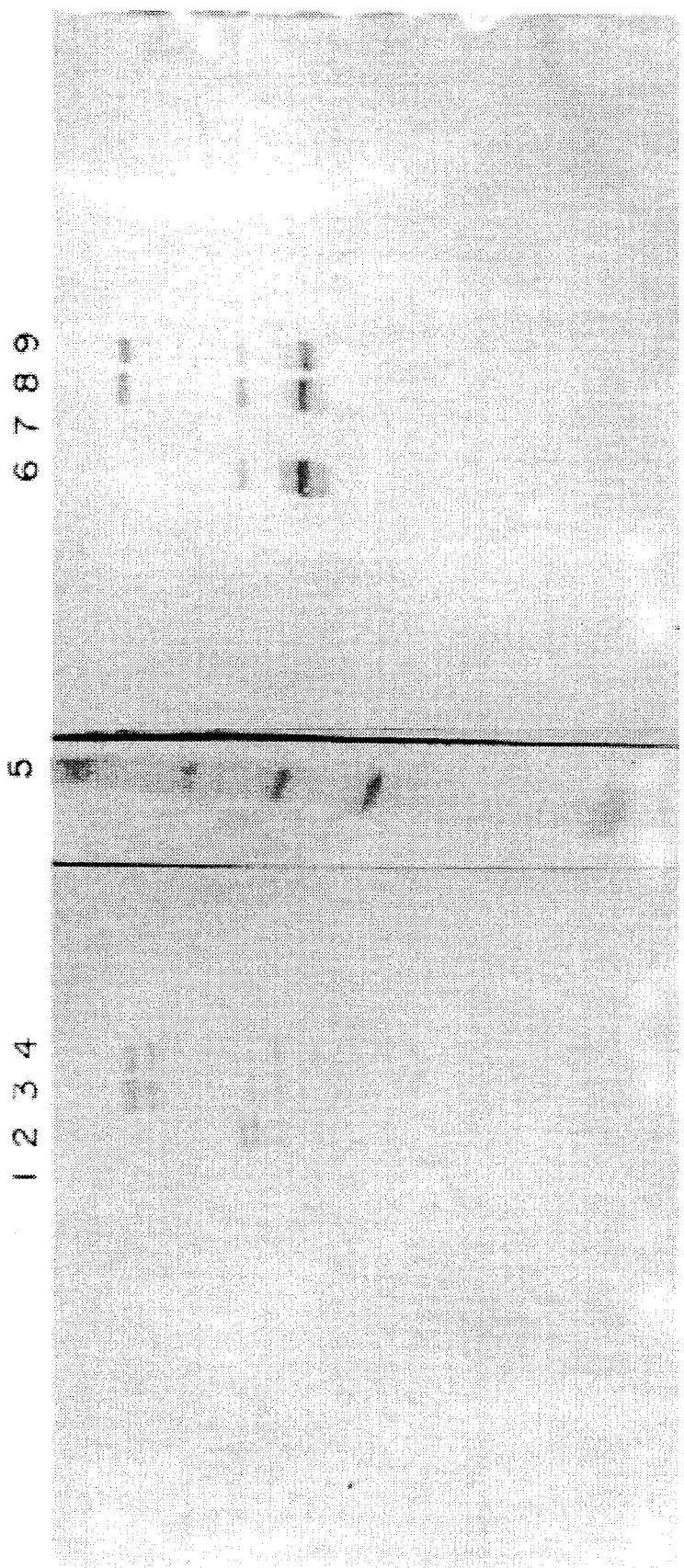
FIG. 1 illustrates Western blots probed with polyclonal antibodies to alpha-1-antitrypsin (A) or boar acrosin (B), demonstrating the formation of a high molecular weight complex between the two proteins. Lanes 1 and 6, proacrosin (~5 ug) autoactivated to acrosin; Lanes 2 and 7, alpha-1-antrypsin (~2 ug); Lanes 3 and 8, alpha-1-antitrypsin (~2 ug)+activated proacrosin (~5 ug) in 0.1M Tris, pH 8.0; Lanes 4 and 9, alpha-1-antitrypsin (~2 ug)+activated proacrosin (~5 ug) in 0.1M Tris, 0.05 M $CaCl_2$, pH 8.0; Lane 5, molecular weight markers.

As noted above, the present invention discloses a method for inhibiting fertilization in warm-blooded animals. Within a preferred embodiment, the contraceptive composition comprises an effective amount of a proteinase inhibitor of the serpin family and a physiologically acceptable carrier or diluent. As described herein, serpins are suitable for use as contraceptives due to their ability to bind to acrosin via a covalent interaction which is not readily reversible under physiological conditions.

A particularly preferred serpin is alpha-1-antitrypsin. Human alpha-1-antitrypsin is a 394 amino acid glycoprotein which has a primary physiological role of inhibiting the action of leucocyte elastase in the lung, thus preventing tissue damage which would otherwise result from normal defense methanisms against inhaled foreign particles.

Alpha-1-antitrypsin may be purified from plasma (e.g., as described by Crawford, *Arch. Biochem. Biophys.* 156: 215–222, 1973; and Schochat et al., *J. Biol. Chem.* 253: 5630–5634, 1978). However, it is preferred that the protein be produced through the use of recombinant DNA technology. Several researchers, including Kawasaki (U.S. Pat. No. 4,599,311, herein incorporated by reference), Kawasaki and Bell (EP 171,142); Cabezon et al. (*Proc. Natl. Acad. Sci. USA* 81: 6594–6598, 1984); and Courtney (*Proc. Natl. Acad. Sci. USA* 81: 669–673, 1984) have reported the expression of alpha-1-antitrypsin in recombinant microorganisms. Although recombinant alpha-1-antitrypsin may lack the carbohydrate side chains of the natural molecule or include an additional N-terminal methionine residue, these proteins have been shown to be fully active as proteinase inhibitors. A preferred host microorganism is the yeast *Saccharomyces cerevisiae*.

A number of naturally-occurring variants of alpha-1-antitrypsin are known to exist as a result of genetic polymorphism (Carrell et al., *Nature* 298: 329–334, 1982), and additional variants have been produced through genetic engineering. Courtney et al. (*Nature* 313: 149–151, 1985) describe Met (358) to Val and Met (358) to Arg variants. Insley and Kawasaki (EP 155,188) describe the production of AAT variants with Ala, Val, Gly, Phe, Arg or Lys at amino acid 358 or with Lys at amino acid 342. These variant forms may also be used in accordance with the present invention. The Arg (358) mutant is a particularly preferred variant form in this regard.

Other proteinases of the serpin family may also be used within the present invention. Structure of the serpins is reviewed by Carrell and Travis (*TIBS,* January 1985, pp. 20–24). Preferred proteinases include, in addition to alpha-1-antitrypsin, antithrombin III and plasminogen activator inhibitor. Other, non-proteinase members of this group, such as ovalbumin, may be modified through genetic engineering techniques to include a proteinase reactive center, and thereby be converted to a molecule suitable for use as a contraceptive agent. The hallmark of the reactive center is an exposed loop in a constrained configuration (Carrell and Owen, *Nature* 317: 736–738, 1985). This loop contains the active site residue believed to be responsible for determining inhibitory specificity. For use within the present invention, such a structure capable of inhibiting acrosin could be constructed de novo or by directed mutagenesis. The preparation of antithrombin III is disclosed by Bock et al. (U.S. Pat. No. 4,517,294). The preparation of plasminogen activator inhibitor is disclosed by Wun and Reich (*J. Biol. Chem.* 262:3646–3653, 1987).

The contraceptive compositions of the present invention will generally be in the form of a gel, foam, cream, or suppository which is suitable for intravaginal use. Although these compositions may be used alone, it is generally preferred that they be used in combination with a barrier method of contraception in order to realize their maximum effectiveness. For example, a contraceptive composition in the form of a gel is applied to a diaphragm in an amount of about 1 ml to 20 ml, preferably about 10 ml, and the diaphragm inserted prior to coitus.

As noted above, the contraceptive compositions will include a member of the serpin family in combination with a physiologically acceptable carrier or diluent, generally a water-soluble compound. Preferred carriers include polyethylene glycol and polyoxyethylene-polyoxypropylene block copolymers ("poloxamers"). The use of poloxamers in intravaginal contraceptive compositions is disclosed by Vickery et al. (U.S. Pat. No. 4,368,186, herein incorporated by reference). The compositions may further contain additional ingredients, including buffers, antimicrobial agents, or glycerol, which may be added to control viscosity. Water may also be added. In addition, liposomes may be included to stimulate the acrosomal reaction. Alpha-1-antitrypsin or other serpins are included in a concentration suitable to provide the contraceptive effect, preferably between 0.5 mg/ml and 10 mg/ml protein, most preferably about 1 mg/ml to 5 mg/ml protein.

Furthermore, the serpins may be used in combination with other proteins and/or small molecules that inhibit other factors in the fertilization pathway. Accessory molecules suitable for use within the present invention include benzamidine, 4-aminobenzamidine, 4'-nitro-phenyl 4-guanidinobenzoate and others (Beyler and Zaneveld, *J. Reprod. Fertil,* 66: 425–431 1982). The contraceptive compositions may also include inhibitors of hyaluronidase, beta-glucuronidase, and beta-N-acetylglucosaminidase (Joyce et al., *Biology of Reproduction* 35: 336–346, 1986). Contraceptive compositions will be formulated to provide the maximal contraceptive effect combined with minimal hazard of toxicity and irritancy.

In addition to the compositions described above, the serpins described herein may be substituted for other spermicidal agents in devices and compositions known in the art. For example, these proteins may be used in the suppositories disclosed by Kazmiroski et al. (U.S. Pat. No. 4,384,003) or in the disposable diaphragm of Dunn et al. (U.S. Pat. No. 4,589,880).

To summarize the examples which follow, Example 1 describes the production of a representative serpin, alpha-1-antitrypsin. Example 2 illustrates the formation of a covalent complex between alpha-1-antitrypsin and acrosin. Example 3 describes the effect of alpha-1-antitrypsin on in vitro fertilization. Example 4 describes the inhibition of fertilization in viva by alpha-1-antitrypsin.

The following examples are offered by way of illustration, and not by way of limitation.

EXAMPLES

Example 1

Production of Alpha-1-Antitrypsin (AAT)

Recombinant alpha-1-antitrypsin (AAT) was produced in yeast essentially as described by Kawasaki and Bell, ibid.

Cells were harvested by centrifugation, washed with deionized water, and disrupted with a DYNO-MILL cell disruptor. The lysate was diluted with two volumes of cold, deionized water, after which polyethylene glycol 1000 (Dow Chemical) was added to a concentration of 14% (w/v). The lysate was then centrifuged and the supernatant harvested for AAT purification.

DEAE Fast Flow Sepharose (Pharmacia) that had been equilibrated with 20 mM sodium phosphate, pH 6.5, was added to a level of 1 ml of packed gel per 1.00 mg of protein and then harvested by filtration on a sintered glass funnel. The gel was washed with two volumes of sodium phosphate buffer, and the AAT was then eluted from the gel with 0.3M NaCl in sodium phosphate buffer. The eluate was concentrated by hollow fiber filtration (Amicon, H1P10-20 cartridge), and the solvent exchanged to 20 mM sodium phosphate, pH 8.0. This sample was then applied to a Super-Q Sepharose column (Pharmacia, 100 mg protein/ml packed gel) that had been equilibrated with 20 mM sodium phosphate, pH 8.0. The column was first washed with 20 mM sodium phosphate, pH 8.0 (three column volumes) and then eluted stepwise with 0.1M NaCl, 20 mM sodium phosphate, pH 8.0 (two column volumes). The majority of the AAT (which eluted with 0.1M NaCl buffer) was then applied to a Zn-chelating Sepharose 6B column (Pharmacia, 10 mg protein/ml gel) that had been equilibrated with 0.1M NaCl in 20 mM sodium phosphate, pH 8.0. The column was washed with 3 column volumes of 20 mM sodium phosphate buffer, pH 6.0 and then eluted with 0.2M sodium phosphate buffer, pH 8.0. The fractions containing AAT were pooled and concentrated to 50 mg protein/ml on a hollow fiber cartridge and applied to a phenyl-Sepharose column (Pharmacia, 100 mg protein/ml gel). The effluent from this column was directly applied to a S-200 superfine column (Pharmacia, 2% sample volume per bed volume) and chromatographed with phosphate-buffered saline as a mobile phase. Fractions containing AAT were stored at −80° C.

AAT was typically 3% of the soluble lysate protein. The purification procedure resulted in AAT which appeared to be homogeneous by analysis on polyacrylamide gel electrophoresis in NaDodSO$_4$ on a 10% gel system (Laemmli, *Nature* 227: 680–682, 1970). The molecular weight of the protein appeared to be 42,000 Daltons as compared to standard protein markers and was found not to stain with Basic Fuchsin carbohydrate stain for glycoproteins (Zacharius and Zel L, *Anal. Biochem.* 30: 148–156, 1969). The N-terminus was found to be blocked to Edman degradation, and the blocking group was shown to be N-acetylmethionine by mass spectroscopy.

Example 3

Formation of a Covalent Complex Between Alpha-1-Antitrypsin and Acrosin

The effects of alpha-1-antitrypsin on purified acrosin were measured spectrophotometrically using the acrosin substrate N-α-benzoyl-L-arginine ethyl ester (BAEE) essentially as described by Polakoski and Zaneveld (*Methods in Enzymology* 45 (*part B*): 325, 1976). Boar acrosin was combined with AAT in 0.025M Tris, pH 7.0, containing BAEE. A control sample lacked AAT. The absorbance of the reaction mixture was monitored at 253 nm. The amount of AAT tested was sufficient in effecting complete inhibition of acrosin in the test system.

The nature of the reaction between AAT and acrosin was examined by electrophoresis under reducing and denaturing conditions and by Western blot analysis. AAT (2 μg) and activated boar proacrosin (5 μg) were incubated in a buffer containing 0.1M Tris, pH 8.0. Acrosin activity was inhibited 48% in the BAEE assay. Electrophoresis of the reaction mixture on a 12% SDS-polyacrylamide gel, followed by electrotransfer to nitrocellulose and staining with affinity-purified rabbit polyclonal antibody to either AAT or boar acrosin followed by horseradish peroxidase, revealed the formation of a high molecular weight complex containing both the inhibitor and the enzyme. The same analysis performed in the presence of 0.05M CaCl$_2$, a known stabilizer of boar acrosin, revealed essentially identical results (FIG. 1). The presence of this high molecular weight complex under the experimental conditions used indicates that the inhibitor and enzyme combine to form a covalent complex. Moreover, the level of inhibition of BAEE hydrolysis (48%) correlates with the amount of acrosin (~50%) present in the complex (FIG. 1). Thus, all inhibition is accounted for by the formation of a covalent complex.

Example 3

Effect of Alpha-1-Antitrypsin on In Vitro Fertilization

The ability of AAT to inhibit fertilization in vitro was tested using sperm and ova obtained from the hybrid mouse strain B6D2F1. This strain was chosen because a 75% to 85% in vitro fertilization rate is routine and the female mice respond well to superovulatory drugs, producing an average of 30 normal oocytes per animal.

Oocytes were collected from 3- to 4-week-old female B6D2F1 mice. The animals received 5 international units of pregnant mare's serum gonadotropin to initiate follicular growth. After 48 hours, 5 international units of human chorionic gonadotropin were given to effect ovulation. Twelve hours after the last injection, oviducts were removed and oocytes were collected by puncture of the ampullary region, allowing the release of cumulus enclosed oocytes (cumulus clots) into 0.2 ml Fraser's medium (Fraser and Drury, *Biol. Reprod.* 13: 513–518, 1975) under paraffin oil. To randomize oocyte distribution, all cumulus clots were collected into one dish of medium and then placed into the fertilization medium. Oocytes were collected, on average, 15 minutes before sperm addition.

Sperm were collected from the cauda epididymus of 9- to 14-week-old male B6D2F1 mice of proven fertility. Each epididymus contained approximately 40 million sperm with 70% to 80% motility. The cells from one epididymus were placed into 0.2 ml Fraser's medium (containing alpha-1-antitrypsin at 0, 0.01, 0.05, 0.1, 0.2, 0.5 and 1 mM concentrations) under paraffin oil and incubated for one hour at 37° C. in a humidified 5% $CO_2$ in air atmosphere.

After the one-hour capacitation period, the sperm were counted by hemocytometer and 106 sperm cells/ml were added to 0.2 ml Fraser's, medium (free of alpha-1-antitrypsin or containing AAT at the above concentrations) containing cumulus cell-enclosed oocytes. The sperm/oocyte mixture was incubated at 37° C. in a 5% $CO_2$ in air atmosphere for two hours, after which the oocytes were removed and washed three times to remove excess spermatozoa. The washed oocytes were placed into individual 0.01 ml drops of medium under paraffin oil and returned to the 37° C. environment. After an additional three hours of incubation, the oocytes were observed for signs of fertilization (the presence of both the second polar body and two pronuclei). To confirm fertilization, the oocytes were incubated an additional 24 hours and observed for the formation of two-cell embryos.

Figure 2:
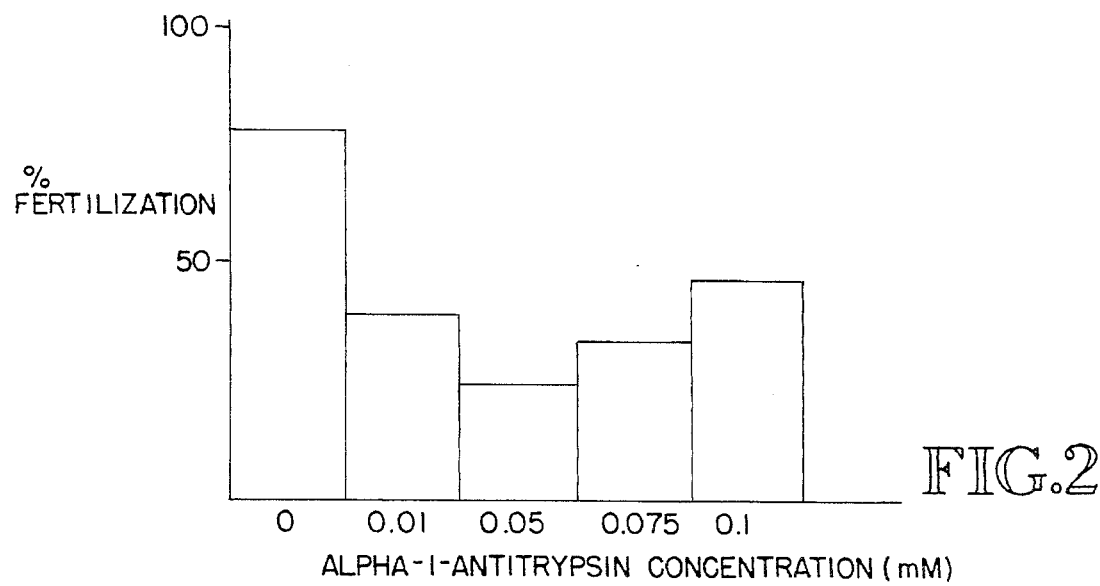
FIGS. 2–4 illustrate the results of fertilization assays demonstrating the inhibitory effect of alpha-1-antitrypsin (AAT) on capacitated sperm.
Figure 3:
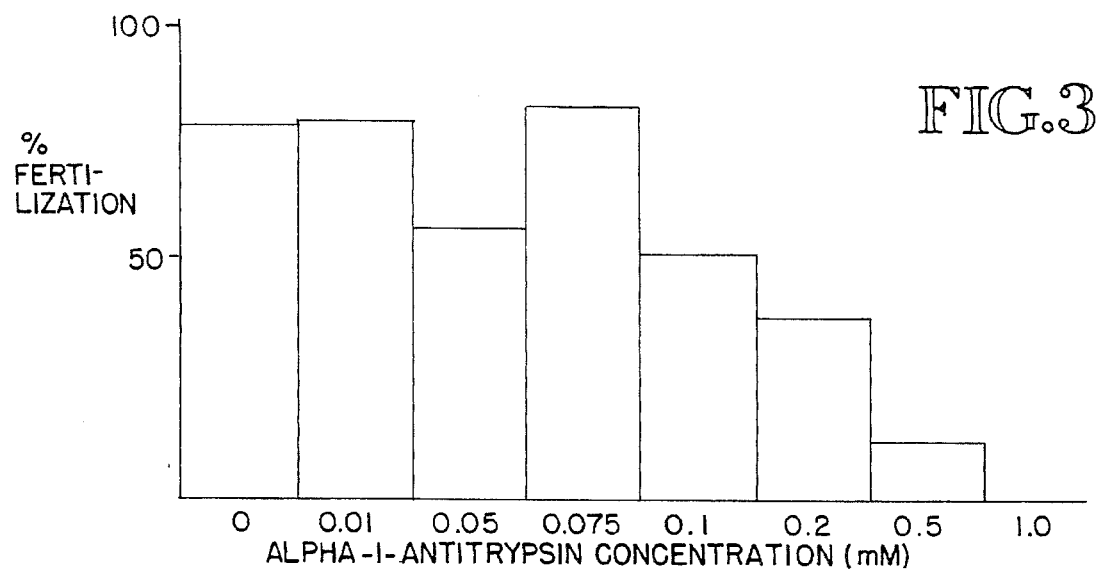
Figure 4:
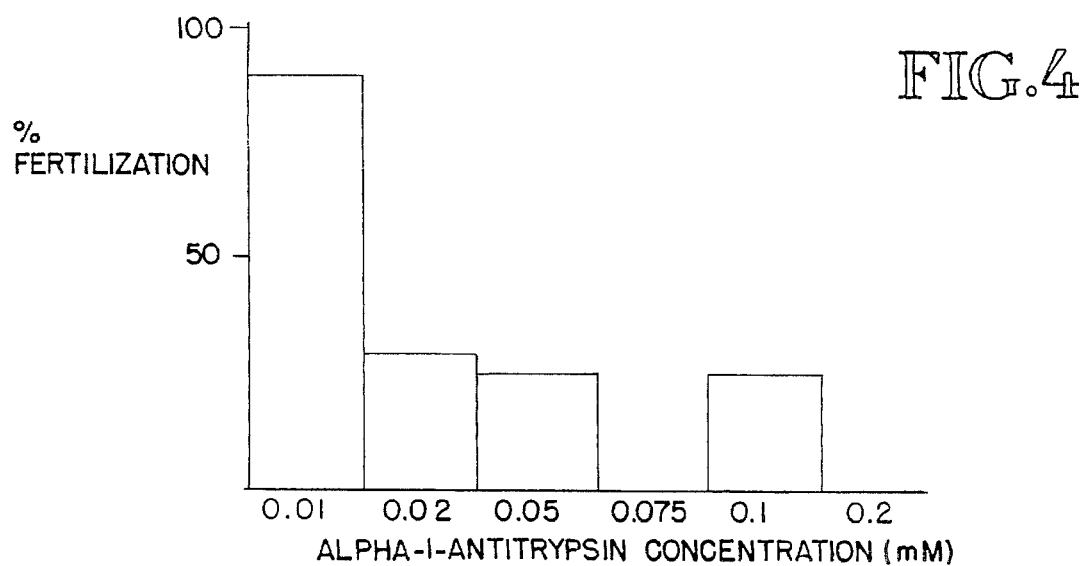

The above experiments were designed to analyze the effective inhibitory concentration of alpha-1-antitrypsin and to detect differences in fertilization rate resulting from the capacitation/acrosome reaction state of the sperm. Thus, sperm capacitated in control medium were used in both control and AAT-containing fertilization media, and sperm capacitated in AAT-containing media were also used in both control and AAT-containing fertilization media. FIGS. 2–4 illustrate the results of the fertilization assays. Data are expressed as percent oocytes with two pronuclei and a second polar body. FIG. 2 presents the results of fertilization studies using sperm capacitated in control medium. The control fertilization rate was 77%, and all concentrations of AAT tested decreased the fertilization rate by about 50%. FIG. 3 presents the results obtained for capacitation in AAT-containing medium and fertilization in control medium. Concentrations of AAT greater than 0.2 mM were effective in blocking fertilization under these conditions. Finally, FIG. 4 presents the results of experiments in which AAT was present in both capacitation and fertilization media. All concentrations of AAT except 0.01 mM were effective in blocking fertilization.

Example 4

Inhibition of Fertilization In Vivo by Alpha-1-Antitrypsin

For in vivo testing, a cream was prepared by dissolving 100 mg of recombinant AAT in 5 ml of phosphate-buffered saline (PBS; obtained from Sigma Chemical Co.). This solution was emulsified with 15 ml of K-Y Jelly (Johnson & Johnson) to give a final AAT concentration of 100 mg/20 ml.

The cream (100 µl) was administered intravaginal to female mice using an Eppendorf pipette prior to copulation. Control females were untreated or received a control cream consisting of 100 mg bovine serum albumin in 5 ml of PBS plus 15 ml of K-Y Jelly. Copulation was confirmed in two of five BSA controls and four of five experimental mice. Mice were sacrificed 12 days after copulation and the number of fetuses was noted. Results, shown in Table 1, indicate that alpha-1-antitrypsin is an effective contraceptive agent.

TABLE 1

|  | Mouse | Number of Fetuses |
| --- | --- | --- |
| BSA Control | 1 | 0 |
|  | 2 | 0 |
|  | 3 | 0 |
|  | 4 | 11 |
|  | 5 | 12 |
| Alpha-1-Antitrypsin | 1 | 0 |
|  | 2 | 0 |
|  | 3 | 0 |
|  | 4 | 0 |
|  | 5 | 0 |

From the foregoing it will be appreciated that, although specific embodiments of the invention have been described herein for purposes of illustration, various modifications may be made without deviating from the spirit and scope of the invention. Accordingly, the invention is not limited except as by the appended claims.

I claim:

1. A method of inhibiting fertilization in warm-blooded animals, comprising:

administering intravaginally to the animal an effective amount of a composition comprising a protein selected from the group consisting of alpha-1-antitrypsin and antithrombin III, acrosin, and a physiologically acceptable carrier or diluent.

2. The method of claim 1 wherein the protein is alpha-1-antitrypsin.

3. The method of claim 2 wherein alpha-1-antitrypsin is present in a concentration of between 0.5 mg/ml and 10 mg/ml.

4. The method of claim 1 wherein the composition is in the form of a gel and is applied in an amount of 1 ml to 20 ml.

5. The method of claim 1 wherein the composition is in the form of a gel, foam, cream, or suppository suitable for intravaginal use.

6. The method of claim 1 wherein the carrier or diluent is polyethylene glycol or a polyoxyethylene-polyoxypropylene block copolymer.

* * * * *

UNITED STATES PATENT AND TRADEMARK OFFICE
CERTIFICATE OF CORRECTION

PATENT NO. : 5,545,615
DATED : August 13, 1996
INVENTOR(S) : Maraganore

It is certified that error appears in the above-indentified patent and that said Letters Patent is hereby corrected as shown below:

In claim 1 at column 8, line 43, please delete "acrosin,".

Signed and Sealed this

Third Day of December, 1996

Attest:

BRUCE LEHMAN

Attesting Officer     Commissioner of Patents and Trademarks